(12) United States Patent
Weiss

(10) Patent No.: US 9,499,600 B2
(45) Date of Patent: Nov. 22, 2016

(54) LONG-ACTING SINGLE-CHAIN INSULIN ANALOGUES

(71) Applicant: CASE WESTERN RESERVE UNIVERSITY, Cleveland, OH (US)

(72) Inventor: Michael Weiss, Moreland Hills, OH (US)

(73) Assignee: Case Western Reserve University, Cleveland, OH (US)

( * ) Notice: Subject to any disclaimer, the term of this patent is extended or adjusted under 35 U.S.C. 154(b) by 0 days.

(21) Appl. No.: 14/440,540

(22) PCT Filed: Nov. 5, 2013

(86) PCT No.: PCT/US2013/068585
§ 371 (c)(1),
(2) Date: May 4, 2015

(87) PCT Pub. No.: WO2014/071405
PCT Pub. Date: May 8, 2014

(65) Prior Publication Data
US 2015/0274803 A1  Oct. 1, 2015

Related U.S. Application Data

(60) Provisional application No. 61/722,350, filed on Nov. 5, 2012.

(51) Int. Cl.
*A61K 38/28* (2006.01)
*C07K 14/62* (2006.01)
*A61P 3/00* (2006.01)
*A61K 38/00* (2006.01)

(52) U.S. Cl.
CPC ............... *C07K 14/62* (2013.01); *A61K 38/00* (2013.01); *A61K 38/28* (2013.01)

(58) Field of Classification Search
CPC ....... A61K 38/28; A61K 38/00; C07K 14/62
See application file for complete search history.

(56) References Cited

U.S. PATENT DOCUMENTS

2010/0099601 A1*  4/2010  Weiss .................... C07K 14/62
514/6.3

* cited by examiner

*Primary Examiner* — Julie Ha
*Assistant Examiner* — Li Ni Komatsu
(74) *Attorney, Agent, or Firm* — Hahn Loeser & Parks LLP

(57) ABSTRACT

A single-chain insulin analog containing a basic side chain at position A8 (Arginine, Histidine, Lysine, or Ornithine), a basic side chain at position B29 (Arginine, Histidine, Lysine, or Ornithine), and a foreshortened C-domain of length 6-11 residues is provided. Residues C1 and C2 of the C-domain have a net negative charge of −1 or −2; C3 is chosen from a group consisting of Gly, Ala, Pro, or Ser; and the remaining C-domain segment is successively derived from the C-domain of IGF-II (RRSR (SEQ ID NO: 18), SRRSR (SEQ ID NO: 17), VSRRSR (SEQ ID NO: 16), RVSRRSR (SEQ ID NO: 15), or SRVSRRSR SEQ ID NO: 13). A method of treating a patient with diabetes mellitus or obesity comprises administering a physiologically effective amount of the insulin analog or a physiologically acceptable salt thereof to a patient.

12 Claims, 8 Drawing Sheets

PROINSULIN

MODEL

Receptor-Binding Studies

2D-NMR Studies

STZ rat studies

LONG-ACTING SINGLE-CHAIN INSULIN ANALOGUES

CROSS REFERENCE TO RELATED APPLICATIONS

This application claims the benefit of U.S. Provisional Application No. 61/722,350 filed on Nov. 5, 2012.

STATEMENT REGARDING FEDERALLY SPONSORED RESEARCH OR DEVELOPMENT

This invention was made with government support under grant numbers DK040949 and DK074176 awarded by the National Institutes of Health. The government has certain rights in the invention.

BACKGROUND OF THE INVENTION

This invention relates to polypeptide hormone analogues that exhibits enhanced pharmaceutical properties, such as increased thermodynamic stability, augmented resistance to thermal fibrillation above room temperature, decreased mitogenicity, and/or altered pharmacokinetic and pharmacodynamic properties, i.e., conferring more prolonged duration of action or more rapid duration of action relative to soluble formulations of the corresponding wild-type human hormone. More particularly, this invention relates to insulin analogues consisting of a single polypeptide chain that contains a novel class of foreshortened connecting (C) domains between A and B domains. Of length 6-11 residues, the C domains of this class consist of an N-terminal acidic element and a C-terminal segment derived from the connecting domain of human IGF-II. The single-chain insulin analogues of the present invention may optionally contain standard or non-standard amino-acid substitutions at other sites in the A or B domains.

The engineering of non-standard proteins, including therapeutic agents and vaccines, may have broad medical and societal benefits. Naturally occurring proteins—as encoded in the genomes of human beings, other mammals, vertebrate organisms, invertebrate organisms, or eukaryotic cells in general—often confer multiple biological activities. A benefit of derivative proteins would be to achieve selective activity, such as decreased binding to homologous cellular receptors associated with an unintended and unfavorable side effect, such as promotion of the growth of cancer cells. Yet another example of a societal benefit would be augmented resistance to degradation at or above room temperature, facilitating transport, distribution, and use. An example of a therapeutic protein is provided by insulin. Wild-type human insulin and insulin molecules encoded in the genomes of other mammals bind to insulin receptors is multiple organs and diverse types of cells, irrespective of the receptor isoform generated by alternative modes of RNA splicing or by alternative patterns of post-translational glycosylation. Wild-type insulin also binds with lower affinity to the homologous Type 1 insulin-like growth factor receptor (IGF-1R).

An example of a further medical benefit would be optimization of the stability of a protein toward unfolding or degradation. Such a societal benefit would be enhanced by the engineering of proteins more refractory than standard proteins with respect to degradation at or above room temperature for use in regions of the developing world where electricity and refrigeration are not consistently available. Analogues of insulin consisting of a single polypeptide chain and optionally containing non-standard amino-acid substitutions may exhibit superior properties with respect to resistance to thermal degradation or decreased mitogenicity. The challenge posed by its physical degradation is deepened by the pending epidemic of diabetes mellitus in Africa and Asia. Because fibrillation poses the major route of degradation above room temperature, the design of fibrillation-resistant formulations may enhance the safety and efficacy of insulin replacement therapy in such challenged regions.

Administration of insulin has long been established as a treatment for diabetes mellitus. A major goal of conventional insulin replacement therapy in patients with diabetes mellitus is tight control of the blood glucose concentration to prevent its excursion above or below the normal range characteristic of healthy human subjects. Excursions below the normal range are associated with immediate adrenergic or neuroglycopenic symptoms, which in severe episodes lead to convulsions, coma, and death. Excursions above the normal range are associated with increased long-term risk of microvascular disease, including retinopathy, blindness, and renal failure.

Insulin is a small globular protein that plays a central role in metabolism in vertebrates. Insulin contains two chains, an A chain, containing 21 residues, and a B chain containing 30 residues. The hormone is stored in the pancreatic β-cell as a $Zn^{2+}$-stabilized hexamer, but functions as a $Zn^{2+}$-free monomer in the bloodstream. Insulin is the product of a single-chain precursor, proinsulin, in which a connecting region (35 residues) links the C-terminal residue of B chain (residue B30) to the N-terminal residue of the A chain (FIG. 1A). A variety of evidence indicates that it consists of an insulin-like core and disordered connecting peptide (FIG. 1B). Formation of three specific disulfide bridges (A6-A11, A7-B7, and A20-B19; FIGS. 1A and 1B) is thought to be coupled to oxidative folding of proinsulin in the rough endoplasmic reticulum (ER). Proinsulin assembles to form soluble $Zn^{2+}$-coordinated hexamers shortly after export from ER to the Golgi apparatus. Endoproteolytic digestion and conversion to insulin occurs in immature secretory granules followed by morphological condensation. Crystalline arrays of zinc insulin hexamers within mature storage granules have been visualized by electron microscopy (EM). The sequence of insulin is shown in schematic form in FIG. 1C. Individual residues are indicated by the identity of the amino acid (typically using a standard three-letter code), the chain and sequence position (typically as a superscript). Pertinent to the present invention is the invention of novel foreshortened C domains of length 6-11 residues in place of the 36-residue wild-type C domain characteristic of human proinsulin.

Fibrillation, which is a serious concern in the manufacture, storage and use of insulin and insulin analogues for the treatment of diabetes mellitus, is enhanced with higher temperature, lower pH, agitation, or the presence of urea, guanidine, ethanol co-solvent, or hydrophobic surfaces. Current US drug regulations demand that insulin be discarded if fibrillation occurs at a level of one percent or more. Because fibrillation is enhanced at higher temperatures, patients with diabetes mellitus optimally must keep insulin refrigerated prior to use. Fibrillation of insulin or an insulin analogue can be a particular concern for such patients utilizing an external insulin pump, in which small amounts of insulin or insulin analogue are injected into the patient's body at regular intervals. In such a usage, the insulin or insulin analogue is not kept refrigerated within the pump apparatus, and fibrillation of insulin can result in blockage of the catheter used to inject insulin or insulin analogue into the body, potentially resulting in unpredictable fluctuations in blood glucose levels or even dangerous hyperglycemia. Insulin exhibits an increase in degradation rate of 10-fold or more for each 10° C. increment in temperature above 25° C.; accordingly, guidelines call for storage at temperatures <30° C. and preferably with refrigeration. Fibrillation of basal insulin analogues formulated as soluble solutions at pH less than 5 (such as Lantus® (Sanofi-Aventis), which contains an unbuffered solution of insulin glargine and zinc ions at pH 4.0) also can limit their self lives due to physical degradation at or above room temperature; the acidic conditions employed in such formulations impairs insulin self-assembly and weakens the binding of zinc ions, reducing the extent to which the insulin analogues can be protected by sequestration within zinc-protein assemblies.

Insulin is susceptible to chemical degradation, involving the breakage of chemical bonds with loss of rearrangement of atoms within the molecule or the formation of chemical bonds between different insulin molecules. Such changes in chemical bonds are ordinarily mediated in the unfolded state of the protein, and so modifications of insulin that augment its thermodynamic stability also are likely to delay or prevent chemical degradation. Insulin is also susceptible to physical degradation. The present theory of protein fibrillation posits that the mechanism of fibrillation proceeds via a partially folded intermediate state, which in turn aggregates to form an amyloidogenic nucleus. In this theory, it is possible that amino-acid substitutions that stabilize the native state may or may not stabilize the partially folded intermediate state and may or may not increase (or decrease) the free-energy barrier between the native state and the intermediate state. Therefore, the current theory indicates that the tendency of a given amino-acid substitution in the two-chain insulin molecule to increase or decrease the risk of fibrillation is highly unpredictable. Models of the structure of the insulin molecule envisage near-complete unfolding of the three-alpha helices (as seen in the native state) with parallel arrangements of beta-sheets formed successive stacking of B-chains and successive stacking of A-chains; native disulfide pairing between chains and within the A-chain is retained. Such parallel cross-beta sheets require substantial separation between the N-terminus of the A-chain and C-terminus of the B-chain (>30 Å), termini ordinarily in close proximity in the native state of the insulin monomer (<10 Å). Marked resistance to fibrillation of single-chain insulin analogues with foreshortened C-domains is known in the art and thought to reflect a topological incompatibility between the splayed structure of parallel cross-beta sheets in an insulin protofilament and the structure of a single-chain insulin analogue with native disulfide pairing in which the foreshortened C-domain constrains the distance between the N-terminus of the A-chain and C-terminus of the B-chain to be unfavorable in a protofilament.

Single-chain insulin analogues might therefore seem to provide a favorable approach toward the design of fibrillation-resistant insulin analogues. However, in the past such analogues have exhibited low activities, which can be 1% or lower relative to wild-type human insulin. (Although Lee, H. C., et al. (2000) claimed that single-chain insulin analogues with wild-type A- and B-domains of length 57 residues or 58 residues exhibit receptor-binding affinities in the range 30-40% relative to human insulin, this publication was retracted in 2009 due to scientific misconduct; in our hands the analogues disclosed by Lee, H. C. et al. exhibit relative affinities of less than 1%.) Affinity might in part be restored by introduction of $Asp^{B10}$, a substitution known in the art to enhance the affinity of insulin for the insulin receptor. We have previously described a 57-residue single-chain insulin containing $Asp^{B10}$ with C-domain linker GGG-PRR (SEQ ID NO: 20). However, use of foreshortened C-domains in conjunction with such substitutions in A-domain and/or B-domain can skew the ratio of binding toward an enhanced ratio of binding to IR-A relative to IR-B as disclosed in U.S. patent application Ser. No. 12/989,399, entitled "Isoform-Specific Insulin Analogues" (incorporated by reference herein). A single-chain insulin analogue with high receptor-binding affinity was described in which the foreshortened C-domain was the 12-residue C-domain of insulin-like growth factor I (IGF-I; sequence GYGSSSR-RAPQT SEQ ID NO: 12), yielding a chimeric protein. However, such chimeric molecules exhibit enhanced relative and absolute affinities for IGF-1R. Such alterations, like those associated with $Asp^{B10}$ and other substitutions at position B10, have elicited broad concern due to possible association with an increased risk of cancer in animals or human patients taking such analogues. This concern is especially marked with respect to basal insulin analogues, i.e., those designed for once-a-day administration with 12-24 hour profile of insulin absorption from a subcutaneous depot and 12-24 hour profile of insulin action.

The present invention was motivated by the medical and societal needs to engineer a basal once-a-day single-chain insulin analogue that combines (i) resistance to degradation with (ii) substantial in vivo hypoglycemic potency with (iii) reduced cross-binding to IGF-1R and (iv) a ratio of affinities for the A- and B isoforms of the insulin receptor that is similar to that of wild-type human insulin. The latter objective reflected the pleitropic functions and target tissues of insulin in the human body. The classical paradigm of insulin action has focused on organ-specific functions of adipocytes (where insulin regulates storage of fuels in the form of tryglyceride droplets), the liver (where insulin regulates the production of glucose via gluconeogenesis and regulates the storage of fuel in the form of glycogen) and muscle (where insulin regulates the influx of glucose from the bloodstream via trafficking to the plasma membrane of GLUT4) as the target tissues of the hormone. Recent research has revealed, however, that insulin has physiological roles in other organs and tissues, such as in the hypothalamus of the brain, wherein insulin-responsive neural circuitry influences hepatic metabolism, appetite, satiety, and possibly the set point for ideal body weight. Although the human genome contains a single gene encoding the insulin receptor, a transmembrane protein containing a cytoplasmic tyrosine-kinase domain, its pre-messenger RNA undergoes alterative splicing to yield distinct A and B isoforms, whose fractional distribution may differ from organ to organ and whose signaling functions may differ within the same cells.

The A and B isoforms (designated IR-A and IR-B) differ in affinity for insulin (affinity for IR-A is twofold higher than affinity for IR-B), and only IR-A (lacking a peptide domain in the alpha subunit encoded by exon 11) binds IGF-II with high affinity. Although insulin analogues are known in the art that differ from wild-type insulin in the ratio of respective affinities for IR-A and IR-B, it is possible that the safety and efficacy of insulin replacement therapy would optimally require administration of an insulin analogue whose ration of affinities for IR-A and IR-B is similar to that of wild-type insulin. Reduced binding of an insulin analogue to IR-A relative to IR-A, for example, might lead to a relative or absolute decrease in the extent of insulin signaling in the brain and in white blood cells, which express a predominance of IR-A receptors. Similarly, reduced binding an insulin analogue to IR-B relative to IR-B, for example, might lead to a relative or absolute decrease in the extent of insulin signaling in to classical target organs that exhibit predominance of IR-B receptors. Such skewed binding affinities might also perturb the cellular function of target cells (such as pancreatic beta-cells) in which IR-A-mediating insulin signaling and IR-B-mediated insulin signaling are thought to mediate different cellular functions that each contribute to proper beta-cell viability and secretory function. Because cancer cells can exhibit over-expression of IR-A, treatment of a patient with an analogue that exhibits enhanced potency of IR-A signaling (relative to wild-type human insulin) may pose a risk of increasing tumor growth. Mitogenic signaling by insulin analogues in cancer cells may be mediated by analogues that exhibit enhanced cross-binding to the mitogenic IGF-1R receptor (relative to wild-type human insulin) or by analogues that exhibit enhanced binding to IR-A (relative to wild-type human insulin) or by analogues that exhibit prolonged residence times on IGF-1R, IR-A, or IR-B (relative to wild-type human insulin). Basic residues near the C-terminus of the B-chain or B-domain (B28-B30), within a C-terminal extension (B31 or B32), or at the equivalent positions of a single-chain insulin analogue (C1 and C2) can enhance cross-binding of an insulin analogue to IGF-1R and thereby enhance mitogenicity.

It would be desirable, therefore, to invent single-chain insulin analogue with negligible mitogenicity and cross-binding to the IGF-1R that nonetheless retains at least a portion of the glucose-lowering effect of wild-type insulin. More generally, there is a need for an insulin analogue that displays increased thermodynamic stability and increased resistance to fibrillation above room temperature while exhibiting a ratio of affinities for the A- and B isoforms of the insulin receptor, and so by implication at least a subset of the multiple organ-specific biological activities of wild-type insulin.

SUMMARY OF THE INVENTION

It is, therefore, an aspect of the present invention to provide single-chain insulin analogues that provide decreased cross-binding to IGF-1R and prolonged duration of action while retaining at least a portion of the glucose-lowering activity of wild-type insulin in rodents following subcutaneous injection. The analogues of the present invention contain Histidine at position B10 and so circumvent concerns regarding carcinogenesis that is associated with an acidic substitution (Aspartic Acid or Glutamic Acid) at this position. It is an additional aspect of the present invention that absolute in vitro affinities of the single-chain insulin analogue for IR-A and IR-B are in the range 5-100% relative to wild-type human insulin and so unlikely to exhibit prolonged residence times in the hormone-receptor complex. The present invention addresses the utility of single-chain insulin analogues that exhibit a ratio of binding affinities for IR-A and IR-B that is similar to that of wild-type human insulin.

The above combination of features is conferred by a novel C-domain design wherein a foreshortened connecting polypeptide (length 6-11 residues) contains an N-terminal acidic element (residues C1 and C2), a flexible joint or hinge (C3), and C-terminal segment derived from the C-domain of IGF-II (C4-$C_n$, where n=6, 7, 8, 9, 10, or 11). The N-terminal acidic element was designed in accordance with studies of two-chain insulin analogues containing 32-residue B-chains wherein the charges of the basic $Arg^{B31}$-$Arg^{B32}$ element of insulin glargine were reversed (U.S. Pat. No. 8,399,407, entitled "Non-Standard Insulin Analogues," incorporated by reference herein). Although not wishing to be constrained by theory, it is envisioned that the two-residue acidic residue introduces unfavorable electrostatic repulsion on binding of the analogue to IGF-1R but is well tolerated by insulin receptor isoforms. Also without wishing to be constrained by theory, it is further envisioned that the IGF-II-derived C-terminal segment of the C-domain of the present invention introduces favorable interactions with insulin receptor isoforms and so functions as an ancillary receptor-binding element rather than a mere tether or space element.

In general, the present invention provides a single-chain insulin analogue comprising a C-domain of the present invention and a modified A-chain containing substitutions at position A8. The present invention thus pertains to a novel class of single-chain insulin analogues wherein the connecting domain (C domain) is of length 6-11 and consists of two elements. The N-terminal element consists of the first two residues (designated C1, C2, and C3, corresponding to residues B31-B33 of an extended insulin B-chain) wherein (i) C1 and C2 contain at least one acidic side chain and a net formal electrostatic charge at pH 7.4 of −1 or −2 and (ii) C3 provides a flexible joint or kink as provided by Glycine, Alanine, Proline or Serine. Examples are, but are not limited to the following dipeptide segments: EEG, AEG, EAG, EDG, DEG, DDG, ADG, ADG, EEA, AEA, EAA, EDA, DEA, DDA, ADA, ADA, EEP, AEP, EAP, EDP, DEP, DDP, ADP, ADP, EES, AES, EAS, EDS, DES, DDS, ADS, or ADS. The C-terminal element contains a peptide segment derived from human insulin-like-growth factor II (IGF-II) whose C domain has sequence SRVSRRSR (SEQ ID NO: 13). Residues C4-$C_n$ (where n=6-11) derive from the C-domain of IGF-II or C-terminal fragments with sequences RVSRRSR (SEQ ID NO: 15), VSRRSR (SEQ ID NO: 16), SRRSR (SEQ ID NO: 17), RRSR (SEQ ID NO: 18), or RSR. These hybrid C domains thus range in length from a minimum of 6 (three residues in the N-terminal element and three residues in the C-terminal element) to a maximum of 11 (three residues in the N-terminal element and eight residues in the C-terminal element). The A-chain contains a basic substitution at A8 (Lysine, Arginine, or Histidine) and a substitution at A21 (Gly, Ala, or Ser) to avoid acid-catalyzed deamidation or other modes of Asn-related chemical degradation. In one example the B-chain also contains substitutions $Lys^{B29}$→Arg to avoid Lys-specific proteolytic cleavage in the course of biosynthesis in yeast.

In another example, the present invention provides a series of single chain insulin (SCI) molecules with linkers of the form $EEGX_n$ (SEQ ID NO: 19) where (i) the EE element at positions C1 and C2 (opposite in charge to the RR element of insulin glargine, the active component of Lantus®) impairs IGF-1R cross-binding, (ii) G provides a flexible hinge, and (iii) $X_n$ derives from the C-domain of IGF-II (sequence SRVSRRSR (SEQ ID NO:13). Use of an IGF-II-derived tether provides the presence of multiple Arg residues (compensating for the negative EE element to provide a net shift in isoelectric point) and hypothesized role in enhancing IR receptor binding. The SCI referred to as Thermalin-basal contains an 8-residue connecting peptide (sequence EEGSRRSR SEQ ID NO: 14). C domains of this length are believed to be compatible with the mechanism of induced fit on receptor binding.

DETAILED DESCRIPTION OF THE INVENTION

Figure 1A:
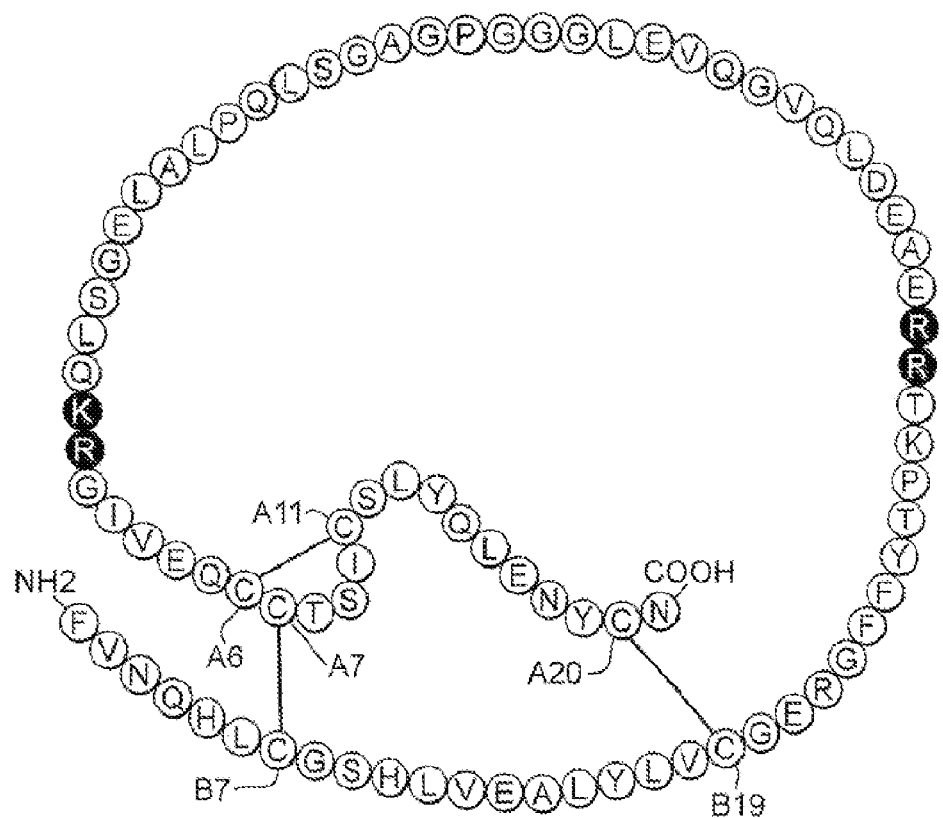
FIG. 1A is a schematic representation of the sequence of human proinsulin including the A- and B-chains and the connecting region shown with flanking dibasic cleavage sites (filled circles) and C-peptide (open circles).
Figure 1B:
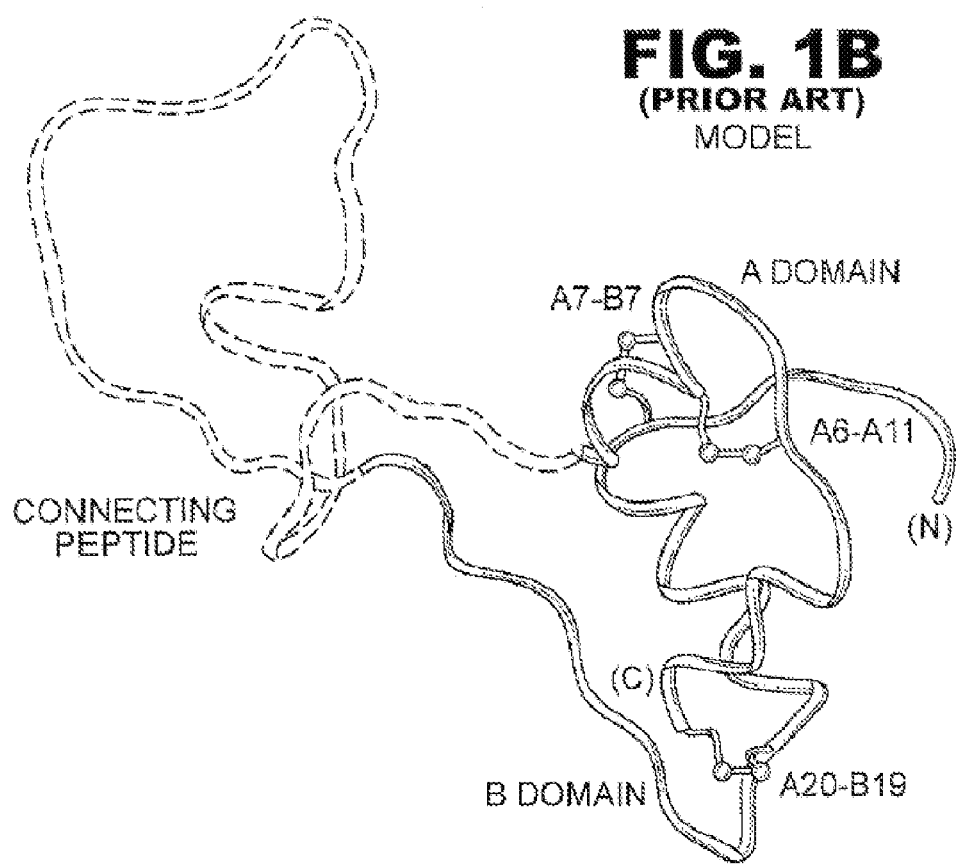
FIG. 1B is a structural model of proinsulin, consisting of an insulin-like moiety and a disordered connecting peptide (dashed line).
Figure 1C:
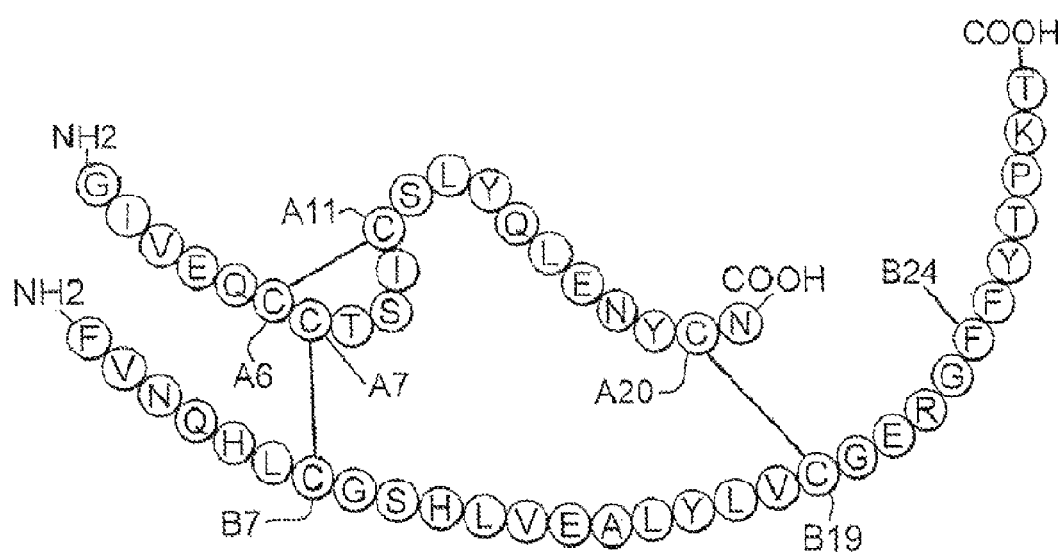
FIG. 1C is a schematic representation of the sequence of human insulin indicating the position of residues B27 and B30 in the B-chain.

The present invention is directed toward a single-chain insulin analogue that provides protracted duration of action, a ratio of IR-A/IR-B receptor-binding affinities similar to that of wild-type insulin with absolute affinities in the range 5-100% (the lower limit chosen to correspond to proinsulin), increased discrimination against IGF-1R, presumed augmented resistance to chemical degradation at position A21 (due to substitution of Asn by Gly, Ala or Ser), presumed augmented resistance to fibrillation above room temperature (due to single-chain topology), and presumed increased thermodynamic activity (due in part to substitution of $Thr^{48}$ by a basic side chain; Arg, Lys, His, Orn).

It is an aspect of at least some examples of the present invention that the isoelectric point of the single-chain analogue is between 6.8 and 7.8 such that a soluble formulation under acidic conditions (pH 3.0-4.5) would be expected to undergo isoelectric precipitation in the subcutaneous depot due to a shift of pH to near neutrality. It is also an aspect of at least some examples of the present invention that the single-chain insulin analogue retain a competence to undergo zinc-ion-dependent formation of protein hexamers analogous to the classical zinc insulin hexamer known in the art as $T_6$ insulin hexamer, $T_3R^f_3$ insulin hexamer, or $R_6$ insulin hexamer.

It is also envisioned that single-chain analogues may also be made with A- and B-domain sequences derived from animal insulins, such as porcine, bovine, equine, and canine insulins, by way of non-limiting examples. In addition or in the alternative, the insulin analogue of the present invention may contain a deletion of residues B1-B3 or may be combined with a variant B chain lacking Lysine (e.g., LysB29 in wild-type human insulin) to avoid Lys-directed proteolysis of a precursor polypeptide in yeast biosynthesis in *Pichia pastoris, Saccharomyces cerevisciae*, or other yeast expression species or strains. The B-domain of the single-chain insulin of the present invention may optionally contain other substitutions, intended to augment thermodynamic stability and receptor-binding activity. It is also envisioned that $Thr^{B27}$, $Thr^{B30}$, or one or more Serine residues in the C-domain may be modified, singly or in combination, by a monosaccharide adduct; examples are provided by O-linked N-acetyl-β-D-galactopyranoside (designated GalNAc-$O^β$-Ser or GalNAc-$O^β$-Thr), O-linked α-D-mannopyranoside (mannose-$O^β$-Ser or mannose-$O^β$-Thr), and/or α-D-glucopyranoside (glucose-$O^β$-Ser or glucose-$O^β$-Thr).

Furthermore, in view of the similarity between human and animal insulins, and use in the past of animal insulins in human patients with diabetes mellitus, it is also envisioned that other minor modifications in the sequence of insulin may be introduced, especially those substitutions considered "conservative." For example, additional substitutions of amino acids may be made within groups of amino acids with similar side chains, without departing from the present invention. These include the neutral hydrophobic amino acids: Alanine (Ala or A), Valine (Val or V), Leucine (Leu or L), Isoleucine (Ile or I), Proline (Pro or P), Tryptophan (Trp or W), Phenylalanine (Phe or F) and Methionine (Met or M). Likewise, the neutral polar amino acids may be substituted for each other within their group of Glycine (Gly or G), Serine (Ser or S), Threonine (Thr or T), Tyrosine (Tyr or Y), Cysteine (Cys or C), Glutamine (Glu or Q), and Asparagine (Asn or N). Basic amino acids are considered to include Lysine (Lys or K), Arginine (Arg or R) and Histidine (His or H). Acidic amino acids are Aspartic acid (Asp or D) and Glutamic acid (Glu or E). Unless noted otherwise or wherever obvious from the context, the amino acids noted herein should be considered to be L-amino acids. Standard amino acids may also be substituted by non-standard amino acids belong to the same chemical class. By way of non-limiting example, the basic side chain Lys may be replaced by basic amino acids of shorter side-chain length (Ornithine, Diaminobutyric acid, or Diaminopropionic acid). Lys may also be replaced by the neutral aliphatic isostere Norleucine (Nle), which may in turn be substituted by analogues containing shorter aliphatic side chains (Aminobutyric acid or Aminopropionic acid).

The amino-acid sequence of human proinsulin is provided, for comparative purposes, as SEQ ID NO: 1.

(human proinsulin)

SEQ ID NO: 1

Phe-Val-Asn-Gln-His-Leu-Cys-Gly-Ser-His-Leu-Val-Glu-Ala-Leu-Tyr-Leu-Val-Cys-Gly-Glu-Arg-Gly-Phe-Phe-Tyr-Thr-Pro-Lys-Thr-Arg-Arg-Glu-Ala-Glu-Asp-Leu-Gln-Val-Gly-Gln-Val-Glu-Leu-Gly-Gly-Gly-Pro-Gly-Ala-Gly-Ser-Leu-Gln-Pro-Leu-Ala-Leu-Glu-Gly-Ser-Leu-Gln-Lys-Arg-Gly-Ile-Val-Glu-Gln-Cys-Cys-Thr-Ser-Ile-Cys-Ser-Leu-Tyr-Gln-Leu-Glu-Asn-Tyr-Cys-Asn

The amino-acid sequence of the A chain of human insulin is provided as SEQ ID NO: 2.

(human A chain)

SEQ ID NO: 2

Gly-Ile-Val-Glu-Gln-Cys-Cys-Thr-Ser-Ile-Cys-Ser-Leu-Tyr-Gln-Leu-Glu-Asn-Tyr-Cys-Asn

The amino-acid sequence of the B chain of human insulin is provided as SEQ ID NO: 3.

(human B chain)

SEQ ID NO: 3

Phe-Val-Asn-Gln-His-Leu-Cys-Gly-Ser-His-Leu-Val-Glu-Ala-Leu-Tyr-Leu-Val-Cys-Gly-Glu-Arg-Gly-Phe-Phe-Tyr-Thr-Pro-Lys-Thr

The amino-acid sequence of single-chain insulin analogues of the present invention are given in SEQ ID NOS: 4-10, corresponding to polypeptides of length 57, 57, 58, 59, 60, 61, and 62.

SEQ ID NO: 4

Phe-Val-Asn-Gln-His-Leu-Cys-Gly-Ser-His-Leu-Val-Glu-Ala-Leu-Tyr-Leu-Val-Cys-Gly-Glu-Arg-Gly-Phe-Phe-Tyr-Thr-Pro-$Xaa_2$-Thr-$Xaa_3$-Glu-Gly-Arg-Ser-Arg-Gly-Ile-Val-Glu-Gln-Cys-Cys-$Xaa_1$-Ser-Ile-Cys-Ser-Leu-Tyr-Gln-Leu-Glu-Asn-Tyr-Cys-$Xaa_4$
Where $Xaa_1$ indicates His, Arg, Lys or Orn; and where $Xaa_2$ is Lys, Arg, or Orn; $Xaa_3$ is Ala, Gly, or Ser; and where $Xaa_4$ is Gly, Ala or Ser.

SEQ ID NO: 5

Phe-Val-Asn-Gln-His-Leu-Cys-Gly-Ser-His-Leu-Val-Glu-Ala-Leu-Tyr-Leu-Val-Cys-Gly-Glu-Arg-Gly-Phe-Phe-Tyr-Thr-Pro-$Xaa_2$-Thr-Glu-$Xaa_3$-Gly-Arg-Ser-Arg-Gly-Ile-Val-Glu-Gln-Cys-Cys-$Xaa_1$-Ser-Ile-Cys-Ser-Leu-Tyr-Gln-Leu-Glu-Asn-Tyr-Cys-$Xaa_4$
Where $Xaa_1$ indictes His, Arg, Lys or Orn; and where $Xaa_2$ is Lys, Arg, or Orn; $Xaa_3$ is Ala, Gly, or Ser; and where $Xaa_4$ is Gly, Ala or Ser.

SEQ ID NO: 6

Phe-Val-Asn-Gln-His-Leu-Cys-Gly-Ser-His-Leu-Val-Glu-Ala-Leu-Tyr-Leu-Val-Cys-Gly-Glu-Arg-Gly-Phe-Phe-Tyr-Thr-Pro-$Xaa_2$-Thr-Glu-Glu-Gly-Arg-Arg-Ser-Arg-Gly-Ile-Val-Glu-Gln-Cys-Cys-$Xaa_1$-Ser-Ile-Cys-Ser-Leu-Tyr-Gln-Leu-Glu-Asn-Tyr-Cys-$Xaa_3$
Where $Xaa_1$ indictes His, Arg, Lys or Orn; and where $Xaa_2$ is Lys, Arg, or Orn; and where $Xaa_3$ is Gly, Ala or Ser.

SEQ ID NO: 7

Phe-Val-Asn-Gln-His-Leu-Cys-Gly-Ser-His-Leu-Val-Glu-Ala-Leu-Tyr-Leu-Val-Cys-Gly-Glu-Arg-Gly-Phe-Phe-Tyr-Thr-Pro-$Xaa_2$-Thr-Glu-Glu-Gly-Ser-Arg-Arg-Ser-Arg-Gly-Ile-Val-Glu-Gln-Cys-Cys-$Xaa_1$-Ser-Ile-Cys-Ser-Leu-Tyr-Gln-Leu-Glu-Asn-Tyr-Cys-$Xaa_3$
Where $Xaa_1$ indictes His, Arg, Lys or Orn; and where $Xaa_2$ is Lys, Arg, or Orn; and where $Xaa_3$ is Gly, Ala or Ser.

SEQ ID NO: 8

Phe-Val-Asn-Gln-His-Leu-Cys-Gly-Ser-His-Leu-Val-Glu-Ala-Leu-Tyr-Leu-Val-Cys-Gly-Glu-Arg-Gly-Phe-Phe-Tyr-Thr-Pro-$Xaa_2$-Thr-Glu-Glu-Gly-Val-Ser-Arg-Arg-Ser-Arg-Gly-Ile-Val-Glu-Gln-Cys-Cys-$Xaa_1$-Ser-Ile-Cys-Ser-Leu-Tyr-Gln-Leu-Glu-Asn-Tyr-Cys-$Xaa_3$
Where $Xaa_1$ indictes His, Arg, Lys or Orn; and where $Xaa_2$ is Lys, Arg, or Orn; and where $Xaa_3$ is Gly, Ala or Ser.

SEQ ID NO: 9

Phe-Val-Asn-Gln-His-Leu-Cys-Gly-Ser-His-Leu-Val-Glu-Ala-Leu-Tyr-Leu-Val-Cys-Gly-Glu-Arg-Gly-Phe-Phe-Tyr-Thr-Pro-$Xaa_2$-Thr-Glu-Glu-Gly-Arg-Val-Ser-Arg-Arg-Ser-Arg-Gly-Ile-Val-Glu-Gln-Cys-Cys-$Xaa_1$-Ser-Ile-Cys-Ser-Leu-Tyr-Gln-Leu-Glu-Asn-Tyr-Cys-$Xaa_3$
Where $Xaa_1$ indictes His, Arg, Lys or Orn; and where $Xaa_2$ is Lys, Arg, or Orn; and where $Xaa_3$ is Gly, Ala or Ser.

-continued

SEQ ID NO: 10

Phe-Val-Asn-Gln-His-Leu-Cys-Gly-Ser-His-Leu-Val-Glu-Ala-Leu-Tyr-Leu-Val-Cys-

Gly-Glu-Arg-Gly-Phe-Phe-Tyr-Thr-Pro-Xaa₂-Thr-Glu-Glu-Gly-Ser-Arg-Val-Ser-Arg-Arg-

Ser-Arg-Gly-Ile-Val-Glu-Gln-Cys-Cys-Xaa₁-Ser-Ile-Cys-Ser-Leu-Tyr-Gln-Leu-Glu-Asn-

Tyr-Cys-Xaa₃

Where Xaa₁ indictes His, Arg, Lys or Orn; and where Xaa₂ is Lys, Arg, or Orn;
and where Xaa₃ is Gly, Ala or Ser.

The following DNA sequence encodes single-chain insulin analogue SCI-59B (see below) with codons optimized for usage patterns in *Pichia pastoris*.

SEQ. ID. NO 11
TTCGTCAATCAACACTTGTGTGGTTCCCACTTGGTTGAGGCATTGTACTT

GGTCTGTGGTGAGAGAGGATTCTTCTACACCCCTAGAACTGAGGAGGGTT

CTAGAAGATCTAGAGGAATCGTCGAGCAATGTTGTAGATCCATTTGTTCC

TTGTACCAATTGGAGAACTACTGCGGATAA

Analogous synthetic genes have been prepared and cloned in *Pichia pastoris* encoding SCI-59A (see below) and derivatives of SCI-59A and SCI-59B containing the additional substitution Glu$^{B13}$→Gln.

Two single-chain insulin analogues of the present invention (designated SCI-59A and SCI-59B) were prepared by biosynthesis of a precursor polypeptide in *Pichia pastoris*; this system secretes a folded protein containing native disulfide bridges with cleavage N-terminal extension peptide. The cleaved single-chain insulin products had length 59, the sum of a 30-residue B-domain, 8-residue C-domain, and 21-residue A-domain. The C-domain sequence was in each case EEGSRRSR (SEQ ID NO: 14) wherein the acidic element (positions C1 and C2; bold) was introduced to impair binding to IGF-1R, Gly (position C3; italics) was introduced as a flexible joint, and an IGF-II C-domain-derived element (positions C4-C8 in the present analog; underlined). SCI-59A contained additional substitutions Thr$^{48}$→His, Asn$^{A21}$→Gly, and Lys$^{B29}$→Arg whereas SCI-59B contained additional substitutions Thr$^{48}$→Arg, Asn$^{A21}$→Gly, and Lys$^{B29}$→Arg (SEQ ID NO: 7). The formal isoelectric point (pI) of SCI-59A was predicted to be shifted toward neutrality by the combined effects of the C-domain sequence (three additional Arginine residues partially offset by two additional Glutamic acid residues) and an additional titratable Histidine at position A8; the substitution of Arg for Lys at B29 was expected to have a negligible effect on the isoelectric point. The formal pI of SCI-59B was predicted to be further shifted toward neutrality by the combined effects of the C-domain sequence (three additional Arginine residues partially offset by two additional Glutamic acid residues as in SCI-59A) and an additional Arg at position A8.

TABLE 1

In Vitro Receptor-Binding Affinities

|  | insulin | SCI-59A | SCI-59B |
|---|---|---|---|
| Human IR-A | 0.026 ± 0.005 | 0.249 ± 0.036 | 0.055 ± 0.008 |
| Human IR-B | 0.058 ± 0.007 | 1.20 ± 0.165 | 0.154 ± 0.021 |
| Human IGF-1R | 3.45 ± 0.54 | 102.3 ± 32.0 | 35.3 ± 7.4 |

Abbreviations: IR-B, splicing isoform B of the insulin receptor; IGF-1R, Type 1 IGF receptor.

Figure 2:
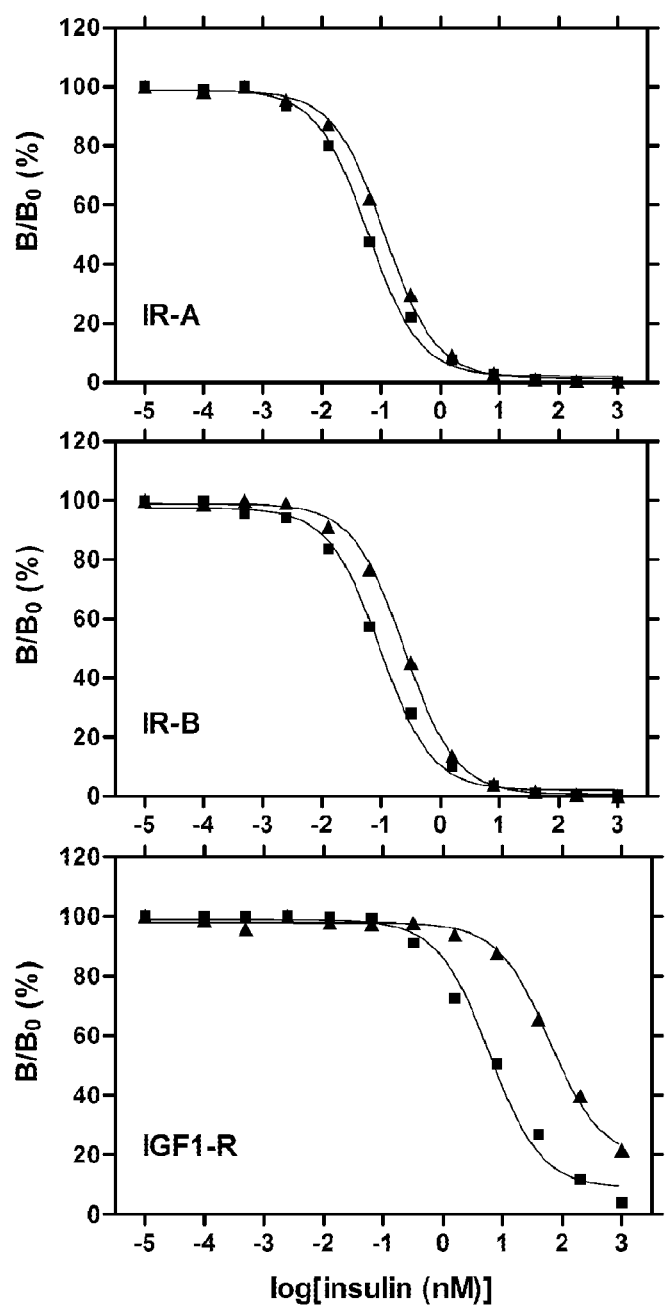
FIG. 2 is a graph showing the results of receptor-binding studies of wild-type human insulin and a single-chain insulin analogue of the present invention (SCI-59B). Top panel, competitive displacement assay employing isoform A of the insulin receptor (IR-A). Middle panel, competitive displacement assay employing isoform B of the insulin receptor (IR-B). Bottom panel, competitive displacement assay employing the Type 1 IGF receptor (IGF-1R). Symbols: human insulin (■) and SCI-59 (▲). Analysis of these data enables estimates of hormone-receptor dissociation constants as provided in Table 1.

Table 1 contains receptor-binding affinities of SCI-59A and SCI-59B in relation to wild-type human insulin. Representative data are provided in FIG. 2. The two single-chain analogues each exhibit very low cross-binding to IGF-1R relative to wild-type insulin. (Relative activity is defined as the ratio of the hormone-receptor dissociation constants of analogue to wild-type human insulin, as measured by a competitive displacement assay using $^{125}$I-human insulin.) SCI-59B exhibits relative affinities for IR-A and IR-B in the target range 5-100% with ratio similar to that of wild-type insulin. By contrast, the IR-A and IR-B affinities of SCI-59A (differing at position A8) are each lower than those of SCI-59B. Whereas the affinity of SCI-59A for IR-A is within the target range (ca. 10%), its affinity for IR-B is at the bottom of the target range (5% within experimental error), resulting in an IR-A/IR-B binding ratio that may be elevated relative to wild-type insulin. These findings suggest that Arg is preferred over His at position A8 in the context of linker EEGSRRSR (SEQ ID NO: 14). The predicted pI of SCI-59B is also closer to that of insulin glargine (which likewise contains an excess of two Arginine residues) than that of SCI-59A.

The protocol for assay of receptor-binding activities was as follows. Microtiter strip plates (Nunc Maxisorb) were incubated overnight at 4° C. with AU5 IgG (100 μl/well of 40 mg/ml in phosphate-buffered saline). Binding data were analyzed by a two-site sequential model. Data were corrected for nonspecific binding (amount of radioactivity remaining membrane associated in the presence of 1 μM human insulin. In all assays the percentage of tracer bound in the absence of competing ligand was less than 15% to avoid ligand-depletion artifacts. Dissociation constants ($K_d$) were determined by fitting to a mathematic model as described by Whittaker and Whittaker (2005. *J. Biol. Chem.* 280: 20932-20936); the model employed non-linear regression with the assumption of heterologous competition (Wang, 1995, *FEBS Lett.* 360: 111-114).

Figure 3:
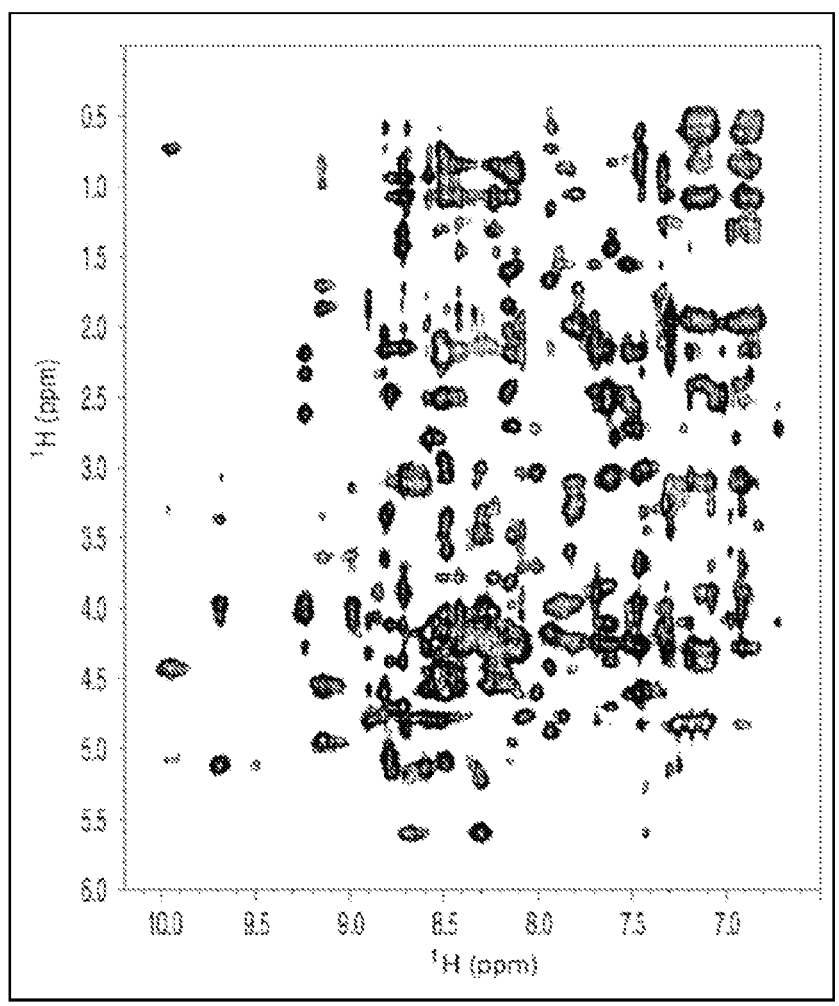
FIG. 3 provides the 2D-NMR spectrum of a single-chain insulin analogue of the present invention (SCI-59B). The spectrum of acquired at pH 3.5 (as in a basal formulation) and 37° C.; the mixing time was 200 ms and field strength 700 MHz.

Structural and biological studies focused on SCI-59B in light of its higher receptor-binding affinity and more favorable predicted isoelectric point. The 2D-NMR NOESY spectrum provided evidence for a folded structure (FIG. 3); the pattern of NOEs and chemical shifts are in accord with prior analysis of a 57-residue single-chain insulin analogue (Hua, Q. X. et al. (2008)).

To evaluate the biological activity and potency of the analogues in an animal model, male Sprague-Dawley rats (mean body mass ~300 grams) were rendered diabetic by treatment with streptozotocin (STZ). Protein solutions containing KP-insulin (insulin Lispro, the active component of Humalog®; Eli Lilly and Co.), insulin Glargine (Lantus®; Sanofi-Aventis), and/or a single-chain insulin of the present invention. A control was provided by injection of protein-free Lilly diluent (obtained from Eli Lilly and Co.) composed of 16 mg glycerin, 1.6 mg meta-cresol, 0.65 mg phenol, and 3.8 mg sodium phosphate pH 7.4. The activity of SCI-59B was evaluated in relation to that of Humulog®

Figure 4:
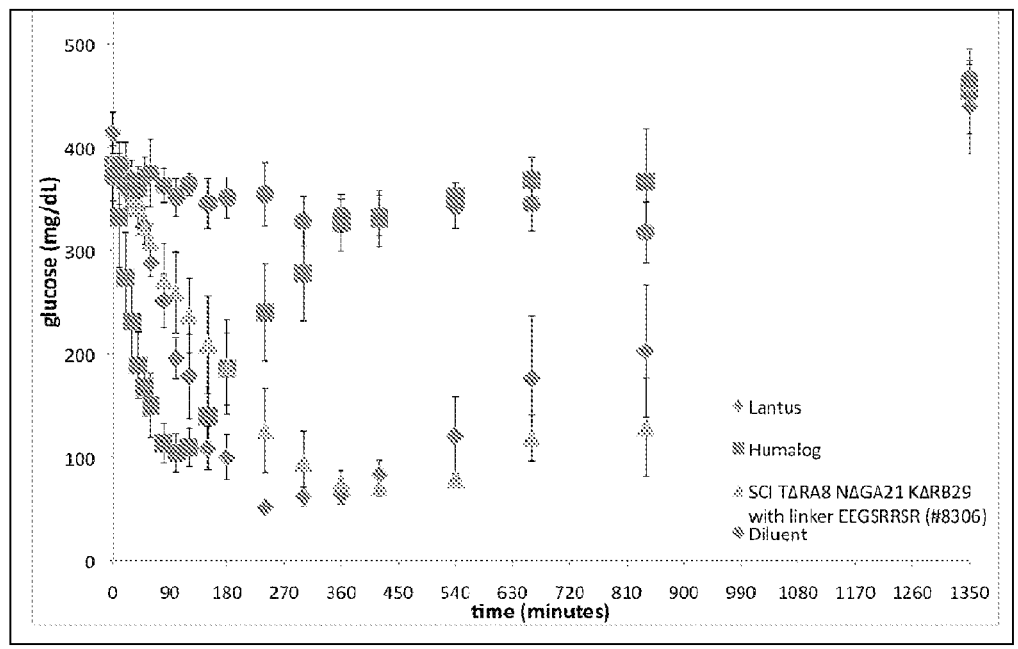
FIG. 4 is a graph showing the results of biological testing of medium-dose insulin analogues in rats (20 μg per rat) rendered diabetic by steptozotocin. Decrease in blood [glucose] with time (min): Humalog® (lispro insulin) (▦), (SCI-59B; ▲) Lantus® (insulin glargine) (◆) and diluent (▦). One unit of each formulation (as U-100) was injected subcutaneously in 5 STZ rats (N=5); error bars indicate standard errors.

(U-100 strength taken from an unexpired commercial vial) and Lantus® (U-100 strength taken from an unexpired commercial vial) as shown in FIG. 4. SCI-57B was formulated according to the formulation of insulin Glargine in Lantus® except that the pH was adjusted in 3.5 (rather than pH 4.0). One unit of each of these formulations were injected subcutaneously, and resulting changes in blood glucose concentration were monitored by serial measurements using a clinical glucometer (Hypoguard Advance Micro-Draw meter). Rats were injected subcutaneously at time t=0 in groups of five (N=5). Blood was obtained from the clipped tip of the tail at time 0 and every 10 minutes up to 360 min. SCI-59B of the present invention were found, under conditions of formulation similar to that of Lantus®, to retain a substantial proportion of the biological activity of insulin glargine and with duration of action similar to or greater than that of Lantus®.

A 59mer SCI was synthesized having the substitutions Arg$^{A8}$, Gly$^{A21}$, Arg$^{B29}$ and having the linker EEGRSSSR (SEQ ID NO: 7). This SCI is referred to as Thermalin-basal or abbreviated as T-b in FIG. 5. Thermodynamic stability was evaluated at 25° C. and pH 4.0 by CD-monitored guanidine denaturation. A free energy of unfolding ($\Delta G_u$) of 3.5(±0.1) kcal/mole was obtained by application of a two-state model, which is higher than the stability of insulin glargine under these conditions (2.7(±0.1) kcal/mole). This increase in free energy ($\Delta\Delta G_u$ 0.7(±0.2) kcal/mole) predicts significantly enhanced chemical stability.

Resistance to fibrillation was probed by gentle agitation in a U-100 formulation at 37 and 45° C. at pH 4.0 in relation to insulin glargine. Whereas Lantus precipitated after 10 days at 37° C. and after 5 days at 45° C., solutions of Thermalin-basal remained clear and without increase in fluorescence of Thioflavin T (a probe of amyloid).

Figure 5A:
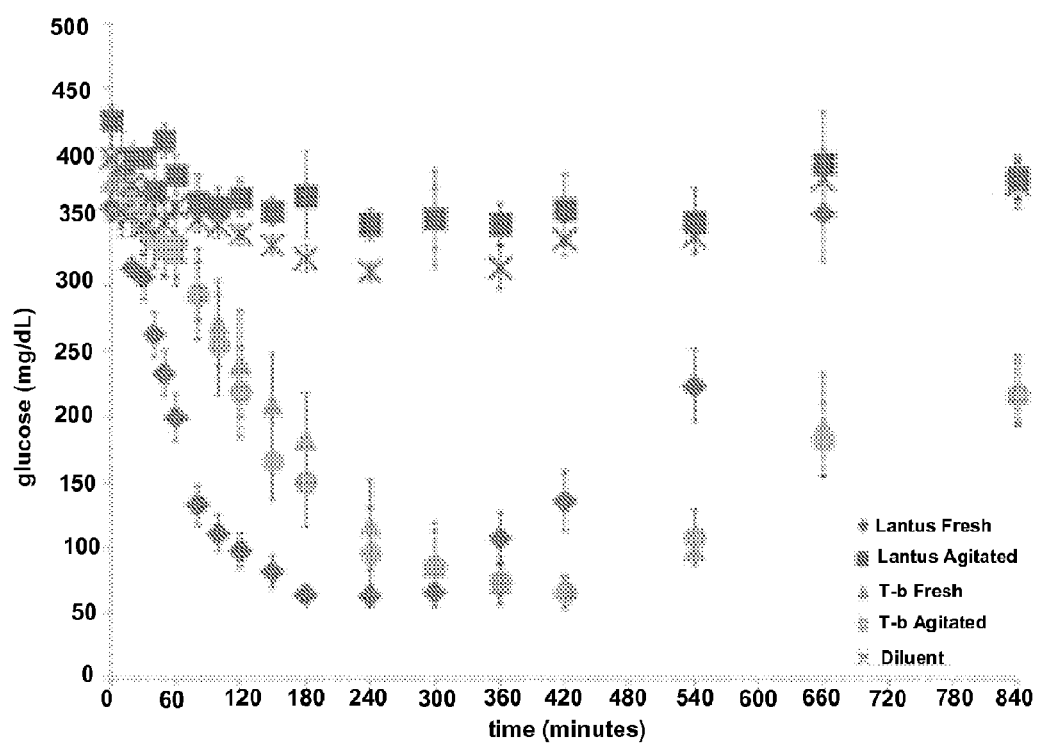
FIG. 5A is a graph showing blood glucose levels over time in Sprague-Dawley rats rendered diabetic by steptozotocin and administered fresh Thermalin-basal (T-b; ▲), heated Thermalin-basal (▦) fresh Lantus® (insulin glargine) (◆) heated Lantus® (insulin glargine) (▦), or diluent control (✖). Heated samples were gently agitated at 37° C. Thermalin-basal was heated for 56 days and Lantus® for 12 days.
Figure 5B:
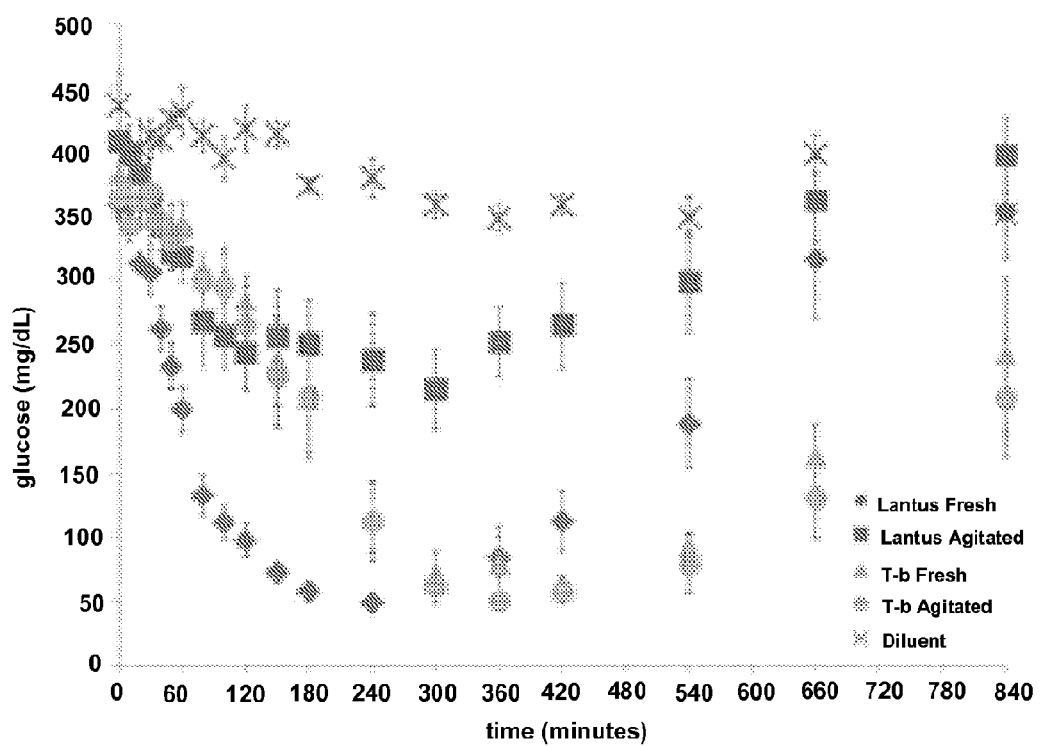
FIG. 5B is a graph showing blood glucose levels over time in Sprague-Dawley rats rendered diabetic by steptozotocin and administered fresh Thermalin-basal (T-b; ▲), heated Thermalin-basal (▦), fresh Lantus® (insulin glargine) (◆) heated Lantus® (insulin glargine) (▦), diluent control (✖). Heated samples were gently agitated at 45° C. Thermalin-basal was heated for 39 days and Lantus® for 6 days.

Potency was tested in Sprague-Dawley rats (ca. 300 g) rendered diabetic by streptozotocin (FIGS. 5A and 5B). Following subcutaneous injection of U-100 (0.6 mM) Thermalin-basal or Lantus® (1 unit per rat; N=5 in the Thermalin-basal group (▲) and N=10 in the Lantus® group (♦)), the resulting reduction and recovery of the blood-glucose concentration (AUC) indicated that the potency of Thermalin-basal is similar to or greater than that of Lantus®. The duration of activity of Thermalin-basal also exceeds that of Lantus®. Retention or loss of potency of Thermalin-basal or Lantus® on gentle agitation at 37 and 45° C. shows that whereas Lantus® rapidly loss its potency (■), Thermalin-basal (●) retained full activity for several weeks under these challenging conditions.

A method for treating a patient with diabetes mellitus comprises administering a single-chain insulin analogue as described herein. It is another aspect of the present invention that the single-chain insulin analogues may be prepared either in yeast (*Pichia pastoris*) or subject to total chemical synthesis by native fragment ligation. The synthetic route of preparation is preferred in the case of non-standard modifications; however, it would be feasible to manufacture a subset of the single-chain analogues containing non-standard modifications by means of extended genetic-code technology or four-base codon technology. It is yet another aspect of the present invention that use of non-standard amino-acid substitutions can augment the resistance of the single-chain insulin analogue to chemical degradation or to physical degradation. We further envision the analogues of the present invention providing a method for the treatment of diabetes mellitus or the metabolic syndrome. The route of delivery of the insulin analogue is by subcutaneous injection through the use of a syringe or pen device.

A pharmaceutical composition may comprise such insulin analogues and which may optionally include zinc. Zinc ions may be included at varying zinc ion: protein ratios, ranging from 2.2 zinc atoms per insulin analogue hexamer to 10 zinc atoms per insulin analogue hexamer. The pH of the formulation is in the range pH 3.0-4.5. In such a formulation, the concentration of the insulin analogue would typically be between about 0.6-5.0 mM; concentrations up to 5 mM may be used in vial or pen; the more concentrated formulations (U-200 or higher) may be of particular benefit in patients with marked insulin resistance. Excipients may include glycerol, glycine, arginine, Tris, other buffers and salts, and anti-microbial preservatives such as phenol and meta-cresol; the latter preservatives are known to enhance the stability of the insulin hexamer. Such a pharmaceutical composition may be used to treat a patient having diabetes mellitus or other medical condition by administering a physiologically effective amount of the composition to the patient.

Based upon the foregoing disclosure, it should now be apparent that the single-chain insulin analogues provided will carry out the objects set forth hereinabove. Namely, these insulin analogues exhibit enhanced resistance to fibrillation while retaining desirable pharmacokinetic and pharmacodynamic features (conferring prolonged action) and maintaining at least a fraction of the biological activity of wild-type insulin. It is, therefore, to be understood that any variations evident fall within the scope of the claimed invention and thus, the selection of specific component elements can be determined without departing from the spirit of the invention herein disclosed and described.

The following literature is cited to demonstrate that the testing and assay methods described herein would be understood by one of ordinary skill in the art.

Glendorf, T., Knudsen, L., Stidsen, C. E., Hansen, B. F., Hegelund, A. C., Sørensen, A. R., Nishimura, E., & Kjeldsen, T. 2012. Systematic evaluation of the metabolic to mitogenic potency ratio for B10-substituted insulin analogues. *PLoS One* 7(2), e29198.

Hohsaka, T., & Sisido, M. 2012. Incorporation of non-natural amino acids into proteins. *Curr. Opin. Chem. Biol.* 6, 809-15.

Hua, Q. X., Nakagawa, S. H., Jia, W., Huang, K., Phillips, N. B., Hu, S. & Weiss, M. A. (2008) Design of an active ultrastable single-chain insulin analog: synthesis, structure, and therapeutic implications. *J. Biol. Chem.* 283, 14703-14716.

Kristensen, C., Andersen, A. S., Hach, M., Wiberg, F. C., Schäffer, L., & Kjeldsen, T. 1995. A single-chain insulin-like growth factor I/insulin hybrid binds with high affinity to the insulin receptor. *Biochem. J.* 305, 981-6.

Lee, H. C., Kim, S. J., Kim, K. S., Shin, H. C., & Yoon, J. W. 2000. Remission in models of type 1 diabetes by gene therapy using a single-chain insulin analogue. *Nature* 408, 483-8. Retraction in: Lee H C, Kim K S, Shin H C. 2009. *Nature* 458, 600.

Phillips, N. B., Whittaker, J., Ismail-Beigi, F., & Weiss, M. A. (2012) Insulin fibrillation and protein design: topological resistance of single-chain analogues to thermal degradation with application to a pump reservoir. *J. Diabetes Sci. Technol.* 6, 277-288.

Sciacca, L., Cassarino, M. F., Genua, M., Pandini, G., Le Moli, R., Squatrito, S., & Vigneri, R. 2010. Insulin analogues differently activate insulin receptor isoforms and post-receptor signalling. *Diabetologia* 53, 1743-53.

Wang, Z. X. 1995. An exact mathematical expression for describing competitive biding of two different ligands to a protein molecule *FEBS Lett.* 360: 111-114.

Whittaker, J., and Whittaker, L. 2005. Characterization of the functional insulin binding epitopes of the full-length insulin receptor. *J. Biol. Chem.* 280: 20932-20936.

What is claimed is:

1. A single-chain insulin analogue comprising the sequence selected from the group consisting of SEQ ID NOs: 4-10.

2. The single-chain insulin analogue of claim 1 comprising the sequence of SEQ ID NO: 7.

3. The single-chain insulin analogue of claim 2, wherein Xaa at position 29 is Arg.

4. The single-chain insulin analogue of claim 3, wherein Xaa at position 59 is Gly.

5. The single-chain insulin analogue of claim 4, wherein Xaa at position 46 is Arg.

6. The single-chain insulin analogue of claim 4, wherein Xaa at position 46 is His.

7. A method of lowering the blood sugar of a patient comprising administering a therapeutically effective amount of a single-chain insulin analogue or a pharmaceutically acceptable salt thereof to the patient, wherein the single-chain insulin analogue comprises the sequence selected from the group consisting of any one of SEQ ID NOs: 4-10.

8. The method of claim 7, wherein the single-chain insulin analogue comprises the sequence of SEQ ID NO: 7.

9. The method of claim 8, wherein Xaa at position 29 of SEQ ID NO: 7 is Arg.

10. The method of claim 9, wherein Xaa at position 59 of SEQ ID NO: 7 is Gly.

11. The method of claim 10, wherein Xaa at position 46 of SEQ ID NO: 7 is Arg.

12. The method of claim 10, wherein Xaa at position 46 of SEQ ID NO: 7 is His.

* * * * *

SEQUENCE LISTING

<160> NUMBER OF SEQ ID NOS: 20

<210> SEQ ID NO 1
<211> LENGTH: 86
<212> TYPE: PRT
<213> ORGANISM: Homo sapiens

<400> SEQUENCE: 1

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu Tyr Gln
65                  70                  75                  80

Leu Glu Asn Tyr Cys Asn
                85

<210> SEQ ID NO 2
<211> LENGTH: 21
<212> TYPE: PRT
<213> ORGANISM: Homo sapiens

<400> SEQUENCE: 2

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 3
<211> LENGTH: 30
<212> TYPE: PRT
<213> ORGANISM: Homo sapiens

<400> SEQUENCE: 3

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 4
<211> LENGTH: 57
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (29)..(29)
<223> OTHER INFORMATION: X is K, R or Ornithine
<220> FEATURE:
<221> NAME/KEY: MISC_FEATURE
<222> LOCATION: (31)..(31)
<223> OTHER INFORMATION: X is A, G, or S
<220> FEATURE:
<221> NAME/KEY: MISC_FEATURE
<222> LOCATION: (44)..(44)
<223> OTHER INFORMATION: X is H, R, K or Ornithine
<220> FEATURE:
<221> NAME/KEY: MISC_FEATURE
<222> LOCATION: (57)..(57)
<223> OTHER INFORMATION: X is G, A or S

<400> SEQUENCE: 4

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Xaa Thr Xaa Glu
            20                  25                  30

Gly Arg Ser Arg Gly Ile Val Glu Gln Cys Cys Xaa Ser Ile Cys Ser
        35                  40                  45

Leu Tyr Gln Leu Glu Asn Tyr Cys Xaa
    50                  55

<210> SEQ ID NO 5
<211> LENGTH: 57
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (29)..(29)
<223> OTHER INFORMATION: X is K, R or Ornithine
<220> FEATURE:
<221> NAME/KEY: MISC_FEATURE
<222> LOCATION: (32)..(32)
<223> OTHER INFORMATION: X is A, G, or S
<220> FEATURE:
<221> NAME/KEY: MISC_FEATURE
<222> LOCATION: (44)..(44)
<223> OTHER INFORMATION: X is H, R, K or Ornithine
<220> FEATURE:
<221> NAME/KEY: MISC_FEATURE
<222> LOCATION: (57)..(57)
<223> OTHER INFORMATION: X is G, A or S

<400> SEQUENCE: 5

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Xaa Thr Glu Xaa
            20                  25                  30

Gly Arg Ser Arg Gly Ile Val Glu Gln Cys Cys Xaa Ser Ile Cys Ser
        35                  40                  45

Leu Tyr Gln Leu Glu Asn Tyr Cys Xaa
    50                  55

<210> SEQ ID NO 6
<211> LENGTH: 58
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (29)..(29)
<223> OTHER INFORMATION: X is K, R or Ornithine
<220> FEATURE:
<221> NAME/KEY: MISC_FEATURE
<222> LOCATION: (45)..(45)
<223> OTHER INFORMATION: X is H, R, K or Ornithine
<220> FEATURE:
<221> NAME/KEY: MISC_FEATURE
<222> LOCATION: (58)..(58)
<223> OTHER INFORMATION: X is G, A or S

<400> SEQUENCE: 6

Phe Val Asn Gln His Leu Cys Gly Ser His Leu Val Glu Ala Leu Tyr
1               5                   10                  15

-continued

```
Leu Val Cys Gly Glu Arg Gly Phe Phe Tyr Thr Pro Xaa Thr Glu Glu
                20                  25                  30

Gly Arg Arg Ser Arg Gly Ile Val Glu Gln Cys Cys Xaa Ser Ile Cys
            35                  40                  45

Ser Leu Tyr Gln Leu Glu Asn Tyr Cys Xaa
        50                  55
```

<210> SEQ ID NO 7
<211> LENGTH: 59
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (29)..(29)
<223> OTHER INFORMATION: X is K, R, or Ornithine
<220> FEATURE:
<221> NAME/KEY: MISC_FEATURE
<222> LOCATION: (46)..(46)
<223> OTHER INFORMATION: X is H, R, K or Ornithine
<220> FEATURE:
<221> NAME/KEY: MISC_FEATURE
<222> LOCATION: (59)..(59)
<223> OTHER INFORMATION: X is G, A or S

<400> SEQUENCE: 7

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Xaa Thr Glu Glu
                20                  25                  30

Gly Ser Arg Arg Ser Arg Gly Ile Val Glu Gln Cys Cys Xaa Ser Ile
            35                  40                  45

Cys Ser Leu Tyr Gln Leu Glu Asn Tyr Cys Xaa
        50                  55
```

<210> SEQ ID NO 8
<211> LENGTH: 60
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (29)..(29)
<223> OTHER INFORMATION: X is K, R, or ornithine
<220> FEATURE:
<221> NAME/KEY: MISC_FEATURE
<222> LOCATION: (47)..(47)
<223> OTHER INFORMATION: X is H, R, K or Ornithine
<220> FEATURE:
<221> NAME/KEY: MISC_FEATURE
<222> LOCATION: (60)..(60)
<223> OTHER INFORMATION: X is G, A or S

<400> SEQUENCE: 8

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Xaa Thr Glu Glu
                20                  25                  30

Gly Val Ser Arg Arg Ser Arg Gly Ile Val Glu Gln Cys Cys Xaa Ser
            35                  40                  45

Ile Cys Ser Leu Tyr Gln Leu Glu Asn Tyr Cys Xaa
        50                  55                  60
```

<210> SEQ ID NO 9

<211> LENGTH: 61
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (29)..(29)
<223> OTHER INFORMATION: X is K, R or Ornithine
<220> FEATURE:
<221> NAME/KEY: MISC_FEATURE
<222> LOCATION: (48)..(48)
<223> OTHER INFORMATION: X is H, R, K or Ornithine
<220> FEATURE:
<221> NAME/KEY: MISC_FEATURE
<222> LOCATION: (61)..(61)
<223> OTHER INFORMATION: X is G, A or S

<400> SEQUENCE: 9

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Xaa Thr Glu Glu
            20                  25                  30

Gly Arg Val Ser Arg Arg Ser Arg Gly Ile Val Glu Gln Cys Cys Xaa
        35                  40                  45

Ser Ile Cys Ser Leu Tyr Gln Leu Glu Asn Tyr Cys Xaa
    50                  55                  60

<210> SEQ ID NO 10
<211> LENGTH: 62
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (29)..(29)
<223> OTHER INFORMATION: X is K, R, or Ornithine
<220> FEATURE:
<221> NAME/KEY: MISC_FEATURE
<222> LOCATION: (49)..(49)
<223> OTHER INFORMATION: X is H, R, K or Ornithine
<220> FEATURE:
<221> NAME/KEY: MISC_FEATURE
<222> LOCATION: (62)..(62)
<223> OTHER INFORMATION: X is G, A or S

<400> SEQUENCE: 10

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Xaa Thr Glu Glu
            20                  25                  30

Gly Ser Arg Val Ser Arg Arg Ser Arg Gly Ile Val Glu Gln Cys Cys
        35                  40                  45

Xaa Ser Ile Cys Ser Leu Tyr Gln Leu Glu Asn Tyr Cys Xaa
    50                  55                  60

<210> SEQ ID NO 11
<211> LENGTH: 180
<212> TYPE: DNA
<213> ORGANISM: Homo sapiens

<400> SEQUENCE: 11
ttcgtcaatc aaacacttgtg tggttcccac ttggttgagg cattgtactt ggtctgtggt     60
gagagaggat tcttctacac ccctagaact gaggagggtt ctagaagatc tagaggaatc    120
gtcgagcaat gttgtagatc catttgttcc ttgtaccaat tggagaacta ctgcggataa    180

```
<210> SEQ ID NO 12
<211> LENGTH: 12
<212> TYPE: PRT
<213> ORGANISM: Homo sapiens

<400> SEQUENCE: 12

Gly Tyr Gly Ser Ser Ser Arg Arg Ala Pro Gln Thr
1               5                   10

<210> SEQ ID NO 13
<211> LENGTH: 8
<212> TYPE: PRT
<213> ORGANISM: Homo sapiens

<400> SEQUENCE: 13

Ser Arg Val Ser Arg Arg Ser Arg
1               5

<210> SEQ ID NO 14
<211> LENGTH: 8
<212> TYPE: PRT
<213> ORGANISM: Artificial Sequence
<220> FEATURE:
<223> OTHER INFORMATION: synthetic construct

<400> SEQUENCE: 14

Glu Glu Gly Ser Arg Arg Ser Arg
1               5

<210> SEQ ID NO 15
<211> LENGTH: 7
<212> TYPE: PRT
<213> ORGANISM: Homo sapiens

<400> SEQUENCE: 15

Arg Val Ser Arg Arg Ser Arg
1               5

<210> SEQ ID NO 16
<211> LENGTH: 6
<212> TYPE: PRT
<213> ORGANISM: Homo sapiens

<400> SEQUENCE: 16

Val Ser Arg Arg Ser Arg
1               5

<210> SEQ ID NO 17
<211> LENGTH: 5
<212> TYPE: PRT
<213> ORGANISM: Homo sapiens

<400> SEQUENCE: 17

Ser Arg Arg Ser Arg
1               5

<210> SEQ ID NO 18
<211> LENGTH: 4
<212> TYPE: PRT
<213> ORGANISM: Homo sapiens

<400> SEQUENCE: 18

Arg Arg Ser Arg
1
```

```
<210> SEQ ID NO 19
<211> LENGTH: 11
<212> TYPE: PRT
<213> ORGANISM: Homo sapiens
<220> FEATURE:
<221> NAME/KEY: MISC_FEATURE
<222> LOCATION: (4)..(11)
<223> OTHER INFORMATION: Xaa Xaa Xaa Xaa Xaa Xaa Xaa Xaa is SRVSRRSR,
      RVSRRSR, VSRRSR, SRRSR, RRSR, or RSR

<400> SEQUENCE: 19

Glu Glu Gly Xaa Xaa Xaa Xaa Xaa Xaa Xaa Xaa
1               5                   10

<210> SEQ ID NO 20
<211> LENGTH: 6
<212> TYPE: PRT
<213> ORGANISM: Homo sapiens

<400> SEQUENCE: 20

Gly Gly Gly Pro Arg Arg
1               5
```